United States Patent [19]

Watanabe et al.

[11] 4,182,880
[45] Jan. 8, 1980

[54] 1,8-NAPHTHYRIDINE COMPOUNDS AND PROCESS FOR PREPARING THE SAME

[75] Inventors: Nanao Watanabe, Sakai; Haruhito Akimoto, Osaka, both of Japan

[73] Assignee: Koei Chemical Co., Ltd., Osaka, Japan

[21] Appl. No.: 968,911

[22] Filed: Dec. 13, 1978

[30] Foreign Application Priority Data

Dec. 27, 1977 [JP] Japan ................. 52-159604

[51] Int. Cl.$^2$ .................... C07F 5/02; C07D 487/04
[52] U.S. Cl. ...................... 546/13; 424/256; 546/123
[58] Field of Search ................. 546/13, 123

[56] Refereces Cited

U.S. PATENT DOCUMENTS

| | | | |
|---|---|---|---|
| 3,296,274 | 1/1967 | Stafiej et al. | 546/13 OR |
| 3,813,406 | 5/1974 | Wada et al. | 546/123 OR |
| 3,849,421 | 11/1974 | Nakagome et al. | 546/123 X |
| 3,963,736 | 6/1976 | Nakagome et al. | 546/123 OR |

*Primary Examiner*—John D. Randolph
*Attorney, Agent, or Firm*—Armstrong, Nikaido, Marmelstein & Kubovcik

[57] ABSTRACT

1,8-Naphthyridine compounds and a process for preparing chelated 1,8-naphthyridine derivatives and 1,8-naphthyridine derivatives which are pharmacautically useful compounds. Chelated 1,8-naphthyridine derivatives of the general formula [I]:

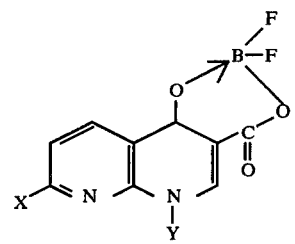

wherein X and Y are independently a lower alkyl group, are prepared by subjecting a compound of the general formula [II]:

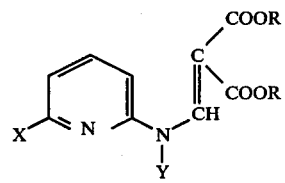

wherein X and Y are as defined above and R is a lower alkyl group, to ring-closing condensation in the presence of boron trifluoride and/or a boron trifluoride complex at an elevated temperature, and 1,8-naphthyridine derivatives of the general formula [III]:

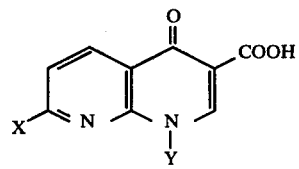

wherein X and Y are as defined above, are prepared by treating the chelated 1,8-naphthyridine derivatives with water and/or an alcohol. The desired products can be readily obtained in high yields. The chelated compounds are novel compounds.

22 Claims, No Drawings

1,8-NAPHTHYRIDINE COMPOUNDS AND PROCESS FOR PREPARING THE SAME

BACKGROUND OF THE INVENTION

The present invention relates to novel chelated 1,8-naphthyridine derivatives and a process for preparing the chelated 1,8-naphthyridine derivatives and 1,8-naphthyridine derivatives. More particularly the invention relates to chelated 1,8-naphthyridine derivatives having the following general formula [I]:

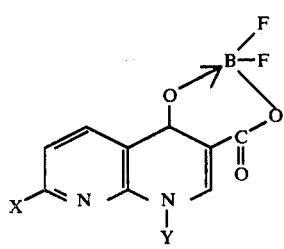

wherein X and Y are independently a lower alkyl group, and a process for preparing the chelated 1,8-naphthyridine derivatives [I] and 1,8-naphthyridine derivatives having the following general formula [III]:

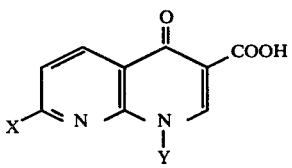

wherein X and Y are as defined above, from compounds as the starting materials having the following general formula [II]:

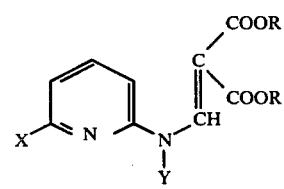

wherein X and Y are as defined above and R is a lower alkyl group.

The 1,8-naphthyridine derivatives of the general formula [III] are substances useful as pharmaceuticals. Particularly a compound of the general formula [III] wherein X is methyl group and Y is ethyl group is a useful antibacterial substance which is described in the Japanese Pharmacopoeia as nalidixic acid.

There are known various processes for preparing nalidixic acid, i.e. 1-ethyl-7-methyl-4-oxo-1,8-naphthyridine-3-carboxylic acid.

U.S. Pat. No. 3,590,036 discloses a process for preparing nalidixic acid by ethylating a compound (A) with ethyl iodide and hydrolyzing the resulting compound (B) as shown in the following scheme.

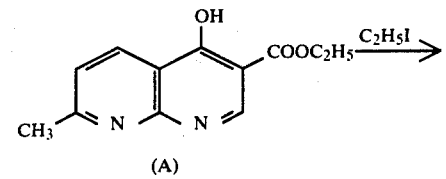

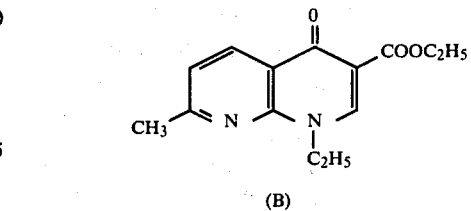

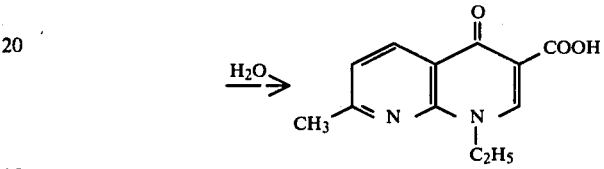

However, according to this process, the yield of the compound (B) is only 27% by mole as described in Example 16 of the Patent.

U.S. Pat. No. 3,590,036 also discloses a process for preparing nalidixic acid by ethylating a compound (C) with ethyl iodide or diethyl sulfate as shown in the following scheme.

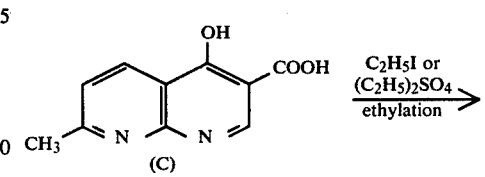

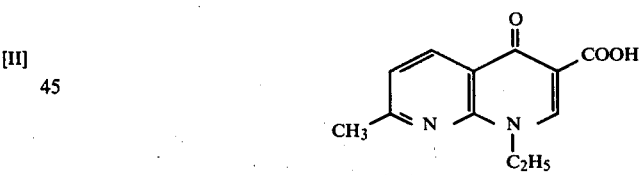

In case of conducting the ethylation with expensive ethyl iodide, even if expensive ethyl iodide is employed in large excess, e.g. in an amount of 3.1 times the stoichiometric quantity, the yield of nalidixic acid is 56% by mole. Even if the reaction is conducted in an excessive manner, for instance, even if the reaction is conducted for 5 days under reflux by employing a larger excess of ethyl iodide, i.e. in an amount of 6.1 times the stoichiometric quantity, the yield is at most 66% by mole. In case of conducting the ethylation with diethyl sulfate, not only the process is dangerous due to the toxicity of the ethylating agent, but also the yield is at most 48% by mole.

In U.S. Pat. No. 3,813,406, there is disclosed a process in which nalidixic acid is directly prepared by ring-closing condensation of, in the presence of polyphosphoric acid, a compound of the following formula:

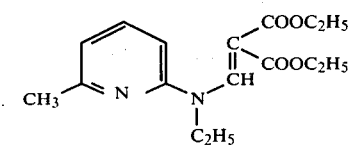

SUMMARY OF THE INVENTION

It has now been found that when the compounds of the general formula [II] are heated in the presence of boron trifluoride and/or a boron trifluoride complex, chelated 1,8-naphthyridine derivatives are formed.

The present invention provides chelated 1,8-naphthyridine derivatives having the following general formula [I]:

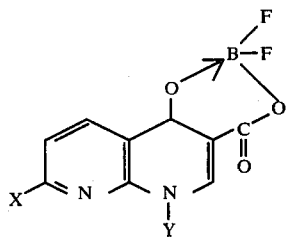

wherein X and Y are independently a lower alkyl group, and a process for preparing the chelated 1,8-naphthyridine derivatives of the general formula [I] which comprises subjecting a compound having the following general formula [II]:

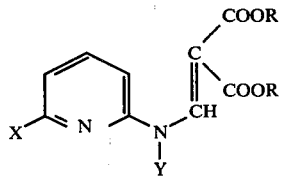

wherein X and Y are as defined above and R is a lower alkyl group, to ring-closing condensation in the presence of boron trifluoride and/or a boron trifluoride complex at an elevated temperature. The present invention also provides a process for preparing 1,8-naphthyridine derivatives having the following general formula [III]:

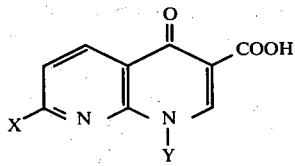

wherein X and Y are as defined above, which comprises treating the chelated 1,8-naphthyridine derivatives of the general formula [I] with water and/or an alcohol.

According to the process of the present invention, chelated 1,8-naphthyridine derivatives [I] which are novel compounds and 1,8-naphthyridine derivatives [III] are readily prepared in high yields.

DETAILED DESCRIPTION

As the starting material, there are employed compounds having the following general formula [II]:

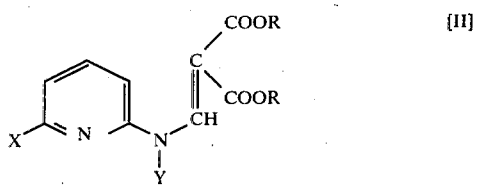

wherein X, Y and R are independently a lower alkyl group, particularly methyl group, ethyl group or propyl group. These malonate compounds are subjected to ring-closing condensation in the presence of boron trifluoride and/or a boron trifluoride complex to give chelated 1,8-naphthyridine derivatives having the following general formula [I]:

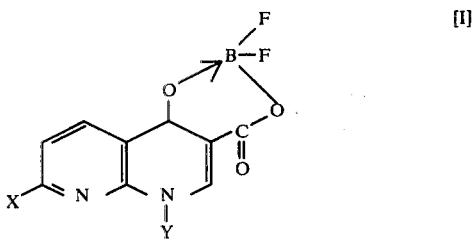

wherein X and Y are as defined above.

The chelated 1,8-naphthyridine derivatives of the general formula [I] are novel compounds, and are useful intermediates of 1,8-naphthyridine derivatives.

The ring-closing condensation is carried out by maintaining a mixture of the malonate compound of the general formula [II] and boron trifluoride and/or a boron trifluoride complex, preferably in the pressence of a solvent, at a temperature of 180° to 250° C., preferably 200° to 240° C. for 1 to 60 minutes, preferably 4 to 40 minutes. In case of carrying out the ring-closing condensation in the presence of a solvent, admixing of the raw materials and the solvent may be conducted in various manners. For instance, there may be applied a manner in which the malonate compound and a solvent are admixed and after heating the mixture to a prescribed temperature, boron trifluoride is blown into or a boron trifluoride complex is added to the mixture, or a manner in which the malonate compound, a boron trifluoride complex and a solvent are admixed at room temperature and the mixture is added dropwise to a solvent which is separately heated to a prescribed temperature.

As the boron trifluoride complex, there can be employed any complexes of boron trifluoride such as ether complexes, e.g. cyclic ether complexes and dialkyl ether complexes, and ketone complexes. Typical examples of the boron trifluoride complex employed in the present invention are tetrahydrofuran, dibutyl ether, diethyl ether and acetone complexes of boron trifluoride. These complexes may be employed singly or in admixture thereof. The amount of boron trifluoride and/or a boron trifluoride complex is selected from 1 to 3 moles, perferably 1 to 1.5 moles, per mole of the malonate compound of the general formula [II].

There may be suitably employed in the present invention any organic solvents which are stable and have a boiling point sufficient to maintain the reaction temperature at 180° to 250° C., for instance, diaryl compounds such as diphenyl and diaryl ether compounds such as diphenyl ether. Diphenyl ether and a mixture of diphenyl ether and diphenyl ether and diphenyl are preferable, since they are easily obtainable. The amount of the solvent to be used is not limited, but from a viewpoint of the operation efficiency, it is desirable to employ the solvent in an amount of not more than 15 parts by weight per one part by weight of the malonate compound.

According to the present invention, 1,8-naphthyridine derivatives having the following general formula [III]:

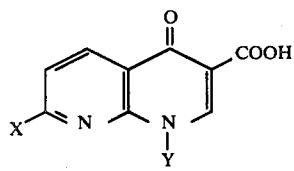

wherein X and Y are as defined above, can be obtained merely by treating the resulting chelated 1,8-naphthyridine derivatives shown by the general formula [I] with water or an alcohol in the absence of or in the presence of an alkali or an acid. In case that the ring-closing condensation has been conducted in the presence of a solvent, the obtained condensation reaction mixture may be subjected to the treatment as it is, or the chelated 1,8-naphthyridine derivatives may be first isolated from the condensation reaction mixture and then subjected to the treatment.

Alcohols such as methanol and ethanol are employed for the treatment in the present invention.

In case of conducting the treatment with water and/or an alcohol in the presence of an alkali, any alkalies can be employed and usually alkali metal hydroxides such as sodium and potassium hydroxides are employed, which are easily obtainable. The amount of the alkali to be used is not limited. For instance, in case of conducting the condensation by using 1 mole of the malonate compound and then treating the resulting chelated 1,8-naphthyridine derivative with a 10% by weight aqueous solution of sodium hydroxide, it is suitable from an operational point of view to employ 1 to 8 liters of the aqueous solution of sodium hydroxide. The alkali treatment is carried out at room temperature or at an elevated temperature. Since the treatment time is shortened, the alkali treatment is preferably conducted with heating, usually at a temperature of not lower than 30° C., preferably at a temperature of 80° to 100° C. After the completion of the alkali treatment, the crystalline 1,8-naphthyridine derivatives of the general formula [III] are obtained by neutralization with an acid. As is clear from the above description, in the present invention the alkali treatment means not only the treatment of the chelated 1,8-naphthyridine derivatives with water and/or an alcohol in the presence of an alkali, but also the acid neutralization treatment of alkali salts of the 1,8-naphthyridine derivatives.

In addition to the alkali treatment by which the desired product can be isolated in high yields, it is also possible to conduct the treatment with water and/or an alcohol in the presence of an acid. The acids employed for this purpose are, for instance, inorganic acids such as sulfuric acid and hydrochloric acid. The acid treatment is conducted at a temperature of not lower than room temperature, preferably at a temperature of 80° to 100° C. After the completion of the acid treatment, the resulting mixture is then allowed to stand or cooled, and if necessary, a large quantity of water is added thereto, to give the crystalline 1,8-naphthyridine derivatives.

The chelated 1,8-naphthyridine derivatives can also be treated merely by employing water and/or an alcohol, as well as the alkali treatment and the acid treatment. In that case, it is preferable to isolate the chelated compound from the condensation reaction mixture and then subject it to the treatment. The treatment is conducted by refluxing a mixture of the chelated compound with water and/or an alcohol, and after allowing the mixture to stand or cooling, the crystalline 1,8-naphthyridine derivatives are obtained by filtering the resulting precipitate.

The thus obtained 1,8-naphthyridine derivatives are of relatively high pure, and may be purified in a usual recrystallization manner to give the product of high quality.

The 1,8-naphthyridine derivatives can be prepared in high yields and in high efficiency according to the process of the present invention which is industrially useful.

The present invention is more particularly described and explained by means of the following Examples.

EXAMPLE 1

At room temperature, 50.19 g. of diethyl N-ethyl-N-(6-methyl-2-pyridyl)aminomethylenemalonate, 25 g. of a heat medium (commercially available under the registered trademark "Dowtherm A" made by Dow Chemical Co.) and 25 g. of boron trifluoride tetrahydrofuran complex were admixed. The resulting mixture was added dropwise over 32 minutes to 400 g. of Dowtherm A stirred and heated to about 230° C. Low boiling substances produced during the reaction were taken out of the reaction system. After the completion of the addition, the reaction mixture was further maintained at about 230° C. for 5 minutes, and was then cooled to room temperature. The precipitate was filtered and washed with petroleum ether to give 43.39 g. of 1-ethyl-7-methyl-4-oxo-1,8-naphthyridine-3-carboxylic acid-BF₂ chelate. The yield was 94.4% by mole.

The results of the elemental analysis, melting point, mass spectrometry and nuclear magnetic resonance analysis were as follows:

Elemental analysis:
Calculated for $C_{12}H_{11}N_2O_3BF_2$: C 51.47%; H 3.96%; N 10.00%; B 3.86%; F 13.57%; Found: C 51.08%; H 4.09%; N 10.26%; B 4.04%; F 12.9%.

Melting point: 270° to 272° C. (decomposition).

Mass spectrometry:
Condition of measurement: 20° C., 130 V.
Parent peak: 280.

Nuclear magnetic resonance analysis:
Condition of measurement: frequency 60 MHz, solvent DMSO-d⁶ internal standard TMS
Chemical shift:
$\delta = 1.87$ p.p.m. (triplet, 3H);
$\delta = 3.14$ p.p.m. (singlet, 3H);
$\delta = 5.21$ p.p.m. (quartet, 2H);
$\delta = 8.20$ p.p.m. (doublet, 1H);
$\delta = 9.11$ p.p.m. (doublet, 1H);
$\delta = 10.00$ p.p.m. (singlet, 1H).

EXAMPLE 2

At room temperature, 10.1 g. of diethyl N-ethyl-N-(6-methyl-2-pyridyl)aminomethylenemalonate, 5 g. of boron trifluoride tetrahydrofuran complex and 5 g. of a mixture of diphenyl ether and diphenyl (2.4:1 by weight) were admixed. The resulting mixture was added dropwise over 25 minutes to 75 g. of a mixture of diphenyl ether and diphenyl (2.4:1 by weight) stirred and maintained at 228° to 231° C., while removing low boiling substances produced during the reaction outside the reaction system. After the completion of the addition, the reaction mixture was further maintained at 228° to 231° C. for 5 minutes, and was then cooled. To the reaction mixture was added 200 g. of a 10% aqueous solution of sodium hydroxide and alkali treatment was carried out on a boiling water bath for 1 hour with stirring. After cooling, an aqueous layer was made acidic by adding acetic acid, and the precipitate was filtered and dried to give 6.6 g. of a crude product. The yield of this crude product was 91.5% by mole. The crude product was recrystallized from 18 g. of dimethylformamide to give 6.54 g. of purified 1-ethyl-7-methyl-4-oxo-1,8-naphthyridine-3-carboxylic acid. The yield of the purified product was 85.4% by mole. The melting point of the purified product was 228° to 230° C., and a mixture of the purified product and authentic nalidixic acid showed no depression of melting point. The infrared absorption spectrum also agreed with that of the authentic nalidixic acid.

EXAMPLE 3

To 80 g. of diphenyl ether was added 10.14 g. of diethyl N-ethyl-N-(6-methyl-2-pyridyl)aminomethylenemalonate, and the mixture was maintained at 225° to 242° C. with stirring. To the mixture was added 6.5 g. of boron trifluoride dibutyl ether complex, and the whole was maintained at the same temperature for 6 minutes, while removing low boiling substances produced during the reaction outside the reaction system, and was then cooled. The alkali treatment was carried out in the same manner as in Example 2 to give 7.18 g. of a crude product. The yield of this crude product was 93.4% by mole. The crude product was recrystallized from 15 g. of dimethylformamide to give 5.93 g. of purified 1-ethyl-7-methyl-4-oxo-1,8-naphthyridine-3-carboxylic acid. The yield of the purified product was 77.1% by mole.

EXAMPLE 4

To 80 g. of diphenyl ether was added 9.9 g. of diethyl N-methyl-N-(6-methyl-2-pyridyl)aminomethylenemalonate, and the mixture was maintained at 225° to 230° C. with stirring. To the mixture was added 5 g. of boron trifluoride tetrahydrofuran complex, and the whole was further maintained at the same temperature for 6 minutes, while removing low boiling substances produced during the reaction outside the reaction system, and was then cooled. The alkali treatment was carried out in the same manner as in Example 2 to give 6.5 g. of a crude product. The yield of this crude product was 87.9% by mole. The crude product was recrystallized from 15 g. of dimethylformamide to give 5.3 g. of purified 1,7-dimethyl-4-oxo-1,8-naphthyridine-3-carboxylic acid. The yield of the purified product was 71.7% by mole.

EXAMPLE 5

To 80 g. of diphenyl ether was added 9.8 g. of diethyl N-n-propyl-N-(6-methyl-2-pyridyl)aminomethylenemalonate, and the mixture was maintained at 225° to 230° C. with stirring. To the mixture was added 5 g. of boron trifluoride tetrahydrofuran complex, and the whole was further maintained at the same temperature for 6 minutes, while removing low boiling substances produced during the reaction outside the reaction system, and was then cooled. The alkali treatment was carried out in the same manner as in Example 2 to give 6.7 g. of a crude product. The yield of this crude product was 88.9% by mole. The crude product was recrystallized from 15 g. of dimethylformamide to give 5.5 g. of purified 1-n-propyl-7-methyl-4-oxo-1,8-naphthyridine-3-carboxylic acid. The yield and the melting point of the purified product were 73.0% by mole and 208° to 209° C., respectively.

EXAMPLE 6

To 80 g. of diphenyl ether was added 9.9 g. of diethyl N-ethyl-N-(6-ethyl-2-pyridyl)aminomethylenemalonate, and the mixture was maintained at 225° to 230° C. with stirring. To the mixture was added 5 g. of boron trifluoride tetrahydrofuran complex. The whole was further maintained at the same temperature for 6 minutes, while removing low boiling substances produced during the reaction outside the reaction system, and was then cooled. The alkali treatment was carried out in the same manner as in Example 2 to give 6.6 g. of a crude product. The yield of this crude product was 86.7% by mole. The crude product was recrystallized from 15 g. of dimethylformamide to give 5.4 g. of 1,7-diethyl-4-oxo-1,8-naphthyridine-3-carboxylic acid. The yield and the melting point of the purified product were 71.0% by mole and 173° to 174° C., respectively.

EXAMPLE 7

To 80 g. of a mixture of diphenyl ether and diphenyl (3:1 by weight) was added 9.74 g. of diethyl N-ethyl-N-(6-methyl-2-pyridyl)aminomethylenemalonate, and the mixture was maintained at 222° to 243° C. with stirring. To the mixture was added 6.5 g. of boron trifluoride diethyl ether complex. The whole was further maintained at the same temperature for 6 minutes, while removing low boiling substances produced during the reaction outside the reaction system, and was then cooled. The alkali treatment was carried out in the same manner as in Example 2 to give 6.46 g. of a crude product. The yield of this crude product was 87.5% by mole. The crude product was recrystallized from 15 g. of dimethylformamide to give 5.62 g. of purified 1-ethyl-7-methyl-4-oxo-1,8-naphthyridine-3-carboxylic acid. The yield of the purified product was 76.1% by mole.

EXAMPLE 8

The procedure of Example 1 was repeated, and 10 g. of the obtained ring-closing condensation product, i.e. 1-ethyl-7-methyl-4-oxo-1,8-naphthyridine-3-carboxylic acid-$BF_2$ chelate was added to 100 ml. of a 5% aqueous solution of sulfuric acid and was treated on a boiling water bath for 1 hour with stirring. The mixture was cooled, and the precipitate was filtered and dried to give 6.7 g. of a crude product. The yield of this crude product was 76.4% by mole. The crude product was recrystallized from 15 g. of dimethylformamide to give 5.69 g. of purified 1-ethyl-7-methyl-4-oxo-1,8-naphthyridine-3-carboxylic acid. The yield of the purified product was 64.9% by mole.

EXAMPLE 9

At room temperature, 9.91 g. of diethyl N-ethyl-N-(6-methyl-2-pyridyl)aminomethylenemalonate, 5 g. of boron trifluoride tetrahydrofuran complex and 5 g. of diphenyl ether was admixed, and the mixture was added dropwise over 15 minutes to 75 g. of diphenyl ether stirred and maintained at 230° to 235° C., while removing low boiling substances produced during the reaction outside the reaction system. After the completion of the addition, the mixture was further maintained at the same temperature for 7 minutes, and was then cooled. The precipitate was filtered, washed with petroleum ether and dried to give 8.23 g. of a crude chelated product. The crude chelated product was added to 200 ml. of water and was treated on a boiling water bath for 1 hour with stirring. The mixture was then cooled and the resulting solid was filtered and dried to give 6.44 g. of a crude product. The yield of this crude product was 85.7% by mole. The crude product was recrystallized from 15 g. of dimethylformamide to give 5.48 g. of purified 1-ethyl-7-methyl-4-oxo-1,8-naphthyridine-3-carboxylic acid. The yield of the purified product was 72.9% by mole.

EXAMPLE 10

At room temperature, 9.80 g. of diethyl N-ethyl-N-(6-methyl-2-pyridyl)aminomethylenemalonate, 5 g. of boron trifluoride tetrahydrofuran complex and 5 g. of diphenyl ether were admixed, and the mixture was added dropwise over 15 minutes to 75 g. of diphenyl ether stirred and maintained at 230° to 235° C., while removing low boiling substances produced during the reaction outside the reaction system. after completion of the addition, the mixture was further maintained at the same temperature for 7 minutes. The reaction mixture was then cooled, and the precipitate was filtered, washed with petroleum ether and dried to give 8.20 g. of a crude chelated product. The crude chelated product was then added to 200 ml. of methanol, and the mixture was reacted under reflux for 1 hour with stirring. After cooling, the resulting precipitate was filtered and dried to give 5.13 g. of a crude product. The yield of this crude product was 69.0% by mole. The crude product was recrystallized from 12 g. of dimethylformamide to give 4.38 g. of purified 1-ethyl-7-methyl-4-oxo-1,8-naphthyridine-3-carboxylic acid. The yield of the purified product was 58.9% by mole.

What we claim is:

1. A chelated 1,8-naphthyridine derivative having the following general formula:

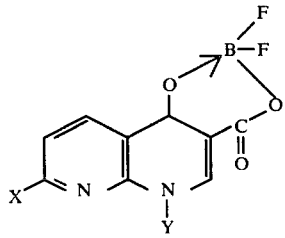

[I]

wherein X and Y are independently a lower alkyl group.

2. The chelated 1,8-naphthyridine derivative of claim 1, wherein said lower alkyl group is an alkyl group having 1 to 3 carbon atoms.

3. The chelated 1,8-naphthyridine derivative of claim 1, wherein said X is methyl group and said Y is ethyl group.

4. A process for preparing chelated 1,8-naphthyridine derivatives having the following general formula:

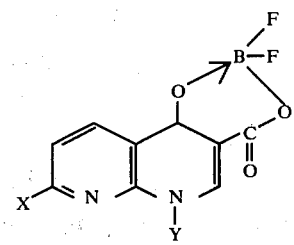

[I]

wherein X and Y are independently a lower alkyl group, which comprises subjecting a compound having the following general formula [II]:

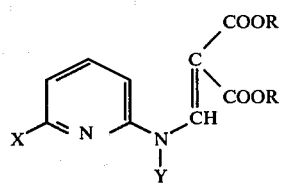

[II]

wherein X and Y are as defined above and R is a lower alkyl group, to ring-closing condensation in the presence of boron trifluoride and/or a boron trifluoride complex at an elevated temperature.

5. The process of claim 4, wherein said ring-closing condensation is carried out at a temperature of 180° to 250° C.

6. The process of claim 4, wherein said ring-closing condensation is carried out in the presence of an organic solvent having a boiling point sufficient to maintain the reaction temperature at 180° to 250° C.

7. The process of claim 6, wherein said organic solvent is a diaryl compound.

8. The process of claim 7, wherein said diaryl compound is diphenyl.

9. The process of claim 6, wherein said organic solvent is a diaryl ether compound.

10. The process of claim 9, wherein said diaryl ether compound is diphenyl ether.

11. The process of claim 6, wherein said organic solvent is a mixture of diphenyl ether and diphenyl.

12. The process of claim 4, wherein said ring-closing condensation is carried out in a manner in which the boron trifluoride and/or the boron trifluoride complex are added to a heated mixture of the compound having the general formula [II] and an organic solvent having a boiling point sufficient to maintain the reaction temperature at 180° to 250° C.

13. The process of claim 4, wherein said ring-closing condensation is carried out in a manner in which the compound having the general formula [II], the boron trifluoride complex and an organic solvent having a boiling point sufficient to maintain the reaction temperature at 180° to 250° C. are admixed at room temperature, and the mixture is added to a separately heated organic solvent having a boiling point sufficient to maintain the reaction temperature at 180° to 250° C.

14. The process of claim 4, wherein said boron trifluoride and/or boron trifluoride complex is employed in an amount of 1 to 3 moles per mole of said compound having the general formula [II].

15. The process of claim 4, wherein said boron trifluoride complex is at least one member selected from the group consisting of cyclic ether, dialkyl ether and ketone complexes of boron trifluoride.

16. The process of claim 4, wherein said boron trifluoride complex is tetrahydrofuran complex of boron trifluoride.

17. The process of claim 4, wherein said X is methyl group and said Y is ethyl group.

18. A process for preparing 1,8-naphthyridine derivatives having the following general formula [III]:

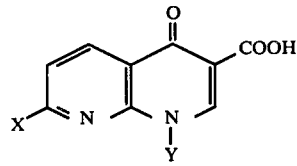

wherein X and Y are independently a lower alkyl group, which comprises subjecting a compound having the following general formula [II]:

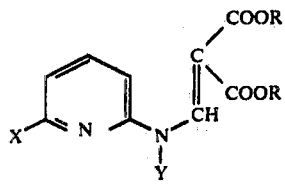

wherein X and Y are as defined above and R is a lower alkyl group, to ring-closing condensation in the presence of boron trifluoride and/or a boron trifluoride complex at an elevated temperature to give a chelated 1,8-naphthyridine derivative having the following general formula [I]:

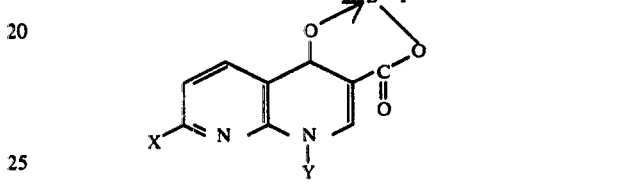

wherein X and Y are as defined above, and treating said chelated 1,8-naphthyridine derivative with water and/or an alcohol.

19. The process of claim 18, wherein the treatment with water and/or an alcohol is carried out at a temperature of 80° to 100° C.

20. The process of claim 18, wherein said alcohol is methanol or ethanol.

21. The process of claim 18, wherein the treatment with water and/or an alcohol is carried out in the presence of an alkali or an acid.

22. The process of claim 18, wherein said X is methyl group and said Y is ethyl group.

* * * * *

UNITED STATES PATENT AND TRADEMARK OFFICE
CERTIFICATE OF CORRECTION

PATENT NO. : 4,182,880
DATED : January 8, 1980
INVENTOR(S) : NANAO WATANABE ET AL.

It is certified that error appears in the above-identified patent and that said Letters Patent are hereby corrected as shown below:

Line 3 of ABSTRACT: Change the spelling of

"pharmacautically" to -- pharmaceutically --;

Column 5, lines 6 - 7: Please correct "a mixture of diphenyl ether and diphenyl ether and diphenyl"

to -- a mixture of diphenyl ether and diphenyl --.

Signed and Sealed this

Seventeenth Day of June 1980

[SEAL]

*Attest:*

SIDNEY A. DIAMOND

*Attesting Officer*  *Commissioner of Patents and Trademarks*